US00PP23994P2

(12) United States Plant Patent
Hartman

(10) Patent No.: US PP23,994 P2
(45) Date of Patent: Oct. 15, 2013

(54) ***CALADIUM* PLANT NAMED 'RIO RED'**

(50) Latin Name: *Caladium×hortulanum*
Varietal Denomination: Rio Red

(76) Inventor: Robert Dale Hartman, Lake Placid, FL (US)

( * ) Notice: Subject to any disclaimer, the term of this patent is extended or adjusted under 35 U.S.C. 154(b) by 113 days.

(21) Appl. No.: 13/374,461

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Rio Red', characterized by its upright and mounding plant habit; short to intermediate plant size; uniform plant habit; vigorous and dense growth habit; lance-type leaves with dark greyed purple-colored venation and dark red and greyed purple-colored interveinal areas, reddish green-colored margins and black-colored leaf petioles; and good landscape performance.

4 Drawing Sheets

Botanical designation: *Caladium×hortulanum.*
Cultivar denomination: 'RIO RED'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'Rio Red'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2008 in Avon Park, Fla. of *Caladium×hortulanum* 'Florida Red Ruffles', disclosed in U.S. Plant Pat. No. 13,136, as the female, or seed, parent with *Caladium×hortulanum* 'Gingerland', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments each segment containing an axillary bud and tuber cortical tissue) in a controlled outdoor nursery environment in Zolfo Springs, Fla. since March, 2010 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Rio Red'.

These characteristics in combination distinguish 'Rio Red' as a new and distinct *Caladium* plant:

1. Upright and mounding plant habit; short to intermediate plant size.
2. Uniform plant habit.
3. Vigorous and dense growth habit.
4. Lance-type leaves with dark greyed purple-colored venation and dark red and greyed purple-colored interveinal areas, reddish green-colored margins and black-colored leaf petioles.
5. Good landscape performance.

Plants of the new *Caladium* differ primarily from plants of the female parent, 'Florida Red Ruffles', in the following characteristics:

1. Plants of the new *Caladium* are taller and more upright than plants of 'Florida Red Ruffles'.
2. Plants of the new *Caladium* grow faster than plants of 'Florida Red Ruffles'.
3. Leaves of plants of the new *Caladium* have sagittate bases whereas leaves of plants of 'Florida Red Ruffles' have obtuse bases.
4. Plants of the new *Caladium* and 'Florida Red Ruffles' differ in leaf petiole color.
5. Plants of the new *Caladium* and 'Florida Red Ruffles' differ in leaf coloration as leaves of plants of 'Florida Red Ruffles' have dark red-colored venation and interveinal areas and green-colored borders.

Plants of the new *Caladium* differ primarily from plants of the male parent, 'Gingerland', in the following characteristics:

1. Plants of the new *Caladium* and 'Gingerland' differ in leaf petiole color.
2. Plants of the new *Caladium* and 'Gingerland' differ in leaf coloration as leaves of plants of 'Gingerland' have white colored venation, white and green-colored interveinal areas with burgundy-colored spots and green-colored borders.

Plants of the new *Caladium* can be compared to plants of *Caladium* 'Red Frills', not patented. In side-by-side comparisons conducted in Avon Park, Fla., plants of the new *Caladium* differed primarily from plants of 'Red Frills' in the following characteristics:

1. Plants of the new *Caladium* were taller and more vigorous than plants of 'Red Frills'.
2. Plants of the new *Caladium* and 'Red Frills' differed in leaf petiole color.
3. Plants of the new *Caladium* and 'Red Frills' differed in leaf coloration as leaves of plants of 'Red Frills' had red-colored venation and interveinal areas and dark green-colored borders.

Plants of the new *Caladium* can also be compared to plants of *Caladium* 'Rosemary', disclosed in U.S. Plant Pat. No. 20,993. In side-by-side comparisons conducted in Zolfo Springs, Fla., plants of the new *Caladium* differed primarily from plants of 'Rosemary' in the following characteristics:

1. Plants of the new *Caladium* were taller and more upright than plants of 'Rosemary'.
2. Plants of the new *Caladium* grew slower than plants of 'Rosemary'.
3. Plants of the new *Caladium* and 'Rosemary' differed in leaf petiole color.
4. Plants of the new *Caladium* and 'Rosemary' differed in leaf coloration as leaves of plants of 'Rosemary' had rose red-colored venation and interveinal areas and variably mottled light and dark green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Rio Red' grown in a 15-cm container in a shadehouse.

The photograph at the top of the second sheet is a side perspective view of typical plants of 'Rio Red' grown in an outdoor nursery.

The photograph at the bottom of the second sheet is a close-up view of typical freshly-harvested tubers and roots of 'Rio Red'.

The photograph at the top of the third sheet is a comparison view of potted plants of 'Rio Red' grown in 15-cm containers, the plant on the right has had its tuber de-eyed and the plant on the left has not had its tuber de-eyed prior to planting.

The photograph at the bottom of the third sheet is a close-up view of a typical inflorescence of 'Rio Red'.

The photograph at the top of the fourth sheet is a comparison view of typical potted plants of the female parent, 'Florida Red Ruffles' (left), 'Rio Red' (center) and the male parent, 'Gingerland' (right).

The photograph at the bottom of the fourth sheet is a comparison view of typical potted plants of 'Red Frills' (left), 'Rio Red' (center) and 'Rosemary' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 28° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old when the photographs and the detailed description were taken. Plants grown in the outdoor nursery were seven months from planting tuber divisions when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Rio Red'.

Parentage:

*Female, or seed, parent.*—*Caladium×hortulanum* 'Florida Red Ruffles', disclosed in U.S. Plant Pat. No. 13,136.

*Male, or pollen, parent.*—*Caladium×hortulanum* 'Gingerland', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to round in shape. Height: About 3.1 cm. Diameter: About 4.9 cm. Texture: Thick and starchy; somewhat brittle. Color: Epidermis, freshly harvested, more brown than 199D and N199D; epidermis, dried tuber, close to 200A to 200B; interior, close to 11C; axillary buds, close to 27D. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded areas.

*Plant and growth habit.*—Upright and mounding plant habit; short to intermediate plant size; inverted triangle; vigorous and dense growth habit; rapid growth rate; petioles and leaves arise from one or more growing points on tubers; petioles mostly upright and leaning outwardly with development.

*Plant height, from soil level to top of foliar plane, shadehouse-grown potted plants.*—About 25 cm to 30 cm.

*Plant height, from soil level to top of inflorescences, shadehouse-grown potted plants.*—About 35 cm.

*Plant diameter or spread, shadehouse-grown potted plants.*—About 41 cm to 45 cm.

*Number of clumps per plant, shadehouse-grown potted plants.*—About four from de-eyed tubers.

*Cataphylls, shadehouse-grown potted plants.*—Length: About 5.4 cm to 9 cm. Width: About 1 cm to 2 cm. Shape: Deltoid. Apex: Acuminate to acute. Base: Sheathing the stem. Color, outer surface: Close to N170D tinged with close to 147C and variably densely streaked with close to 200A tinged with close to 147A; with development, color becoming closer to 200A stained with close to 187A. Color, inner surface: Close to N155C; colors and patterns visible from outer surface.

Foliage description:

*Length, shadehouse-grown potted plants*.—About 15 cm to 21 cm.

*Width, shadehouse-grown potted plants (flattened)*.—About 9.5 cm to 13 cm.

*Shape*.—Ovate.

*Apex*.—Acuminate to acute.

*Base*.—Sagittate, peltate.

*Margin*.—Entire; broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Midrib and primary venation: Close to N186C tinged close to 53C. Areas surrounding midrib and primary venation: Close to 53C tinted with close to N186C. Interveinal areas: Close to 185A tinged with close to 53A; random spots and small sectors, close to N186C and 147A. Borders: Close to 147A tinted with close to N189A. Margins: Close to 187B. Developing leaves, lower surface: Midrib and primary venation: Close to 187B to 187C. Interveinal areas: Close to N186C and 187B; random spots and small sectors, close to 191C tinged with close to 27D and close to 187A. Borders: Close to 189A to 191A. Margins: Close to 187B. Fully expanded leaves, upper surface: Midrib and primary venation: Close to N186C. Areas surrounding midrib and primary venation: Close to N186C tinted with close to 53A. Interveinal areas: Close to 53A and N186C; random spots and small sectors, close to 53A and N186A. Borders: Close to 147A tinted with close to N189A. Margins: Close to 187B. Fully expanded leaves, lower surface: Midrib and primary venation: Close to 187B; distally, close to 191B flecked and streaked with close to 187C. Interveinal areas: Close to N186C and 187B; random spots and small sectors, close to 191B, 187A and close to 191C tinged with close to 27D. Borders: Close to 189A to 191A, occasionally tinted with close to N186C. Margins: Close to 187B.

*Petiole*.—Aspect: Mostly erect and leaning, curving outwardly with development; flexible. Length, shadehouse-grown potted plants: About 18 cm to 24 cm. Diameter, distal, shadehouse-grown potted plants: About 3 mm to 4.5 mm. Diameter, proximal, shadehouse-grown potted plants: About 7 mm to 11.5 mm. Color, shadehouse-grown potted plants: Close to 200A occasionally variably striped with close to N186C or 182C. Wing length, shadehouse-grown potted plants: About 4.5 cm to 8 cm. Wing diameter, shadehouse-grown potted plants: About 7 mm to 11 mm. Wing color, shadehouse-grown potted plants, outer surface: Close to N170D tinged with close to 147C and densely and variably streaked and stippled with close to 200A tinged with close to 147A. Wing color, shadehouse-grown potted plants, inner surface: Close to N155C; outer surface colors and patterns visible.

Inflorescence description: Inflorescences observed on nine-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; sweet jasmine-like with camphor note.

*Natural flowering season/longevity*.—Plants of the new *Caladium* typically flower during the spring or early summer in central Florida; flowers develop about eight to nine weeks after growth commences; inflorescences last about three days before fading; inflorescences persistent.

*Spathe*.—Length: About 11.5 cm; upper open length, about 8 cm and lower closed length, about 3.5 cm. Width, distal: About 5 cm. Width, proximal: About 2.5 cm. Width, at constriction: About 1.6 cm. Shape: Ovate to somewhat obovate. Apex: Acuminate. Base: Tapering to the peduncle. Margin: Entire. Texture, upper and lower surfaces: Smooth, glabrous. Color, front surface, fully opened: Upper two-thirds: Close to 159D with variable occasional spots and streaks close to 53A; occasional spots, close to 146D and 182C to 182D visible from the rear surface; with development, color becoming closer to 199D. Lower one-third: Close to 138C and 147C deeply colored with close to N186A; color does not change with development. Color, rear surface, fully opened: Upper two-thirds: Close to 157D and 157D tinged with close to 161D and variably striped or mottled with close to 182B to 182C. Lower one-third: Close to 185B to 185C and 182C to 182D with variable areas, close to 147B to 147C.

*Spadix*.—Length: About 9 cm. Length, male flower zone: About 5.2 cm. Length, sterile flower zone: About 1.6 cm. Length, female flower zone: About 2.2 cm. Diameter, male flower zone: About 1 cm. Diameter, sterile flower zone: About 7 mm. Diameter, female flower zone: About 1 cm. Shape: Columnar. Apex: Obtuse. Base: Obtuse. Aspect: Upright. Color, mature, male zone: Close to 159C faintly tinged with close to 145D. Color, mature, sterile zone: Close to 159C. Color, mature, female zone: Close to 159A tinged with close to N170D. Male flowers: Quantity per spadix: About 175. Shape: Obovate. Height: About 3 mm. Diameter: About 3 mm. Pollen amount: Moderate. Pollen color: Close to 4C. Female flowers: Quantity per spadix: About 135. Shape: Obovate. Height: About 3 mm. Diameter: About 1 mm. Stigma color: Close to 159A. Ovary color: Close to 159A and 155C.

*Scape*.—Length: About 21.5 cm. Diameter: About 6 mm. Strength: Sturdy; flexible. Aspect: Erect. Texture: Smooth, glabrous; glaucous. Color: Close to 200A tinged with close to 147A; distally, close to 200A tinged with close to 147A and variably streaked with close to 182C and 183C.

*Seeds and fruits*.—Seed and fruit development have not been observed on plants of the new *Caladium*.

Disease & pest tolerance/resistance: Plants of the new *Caladium* have been observed to have above average tolerance to *Xanthomonas* Leaf Spot and average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Rio Red' as illustrated and described.

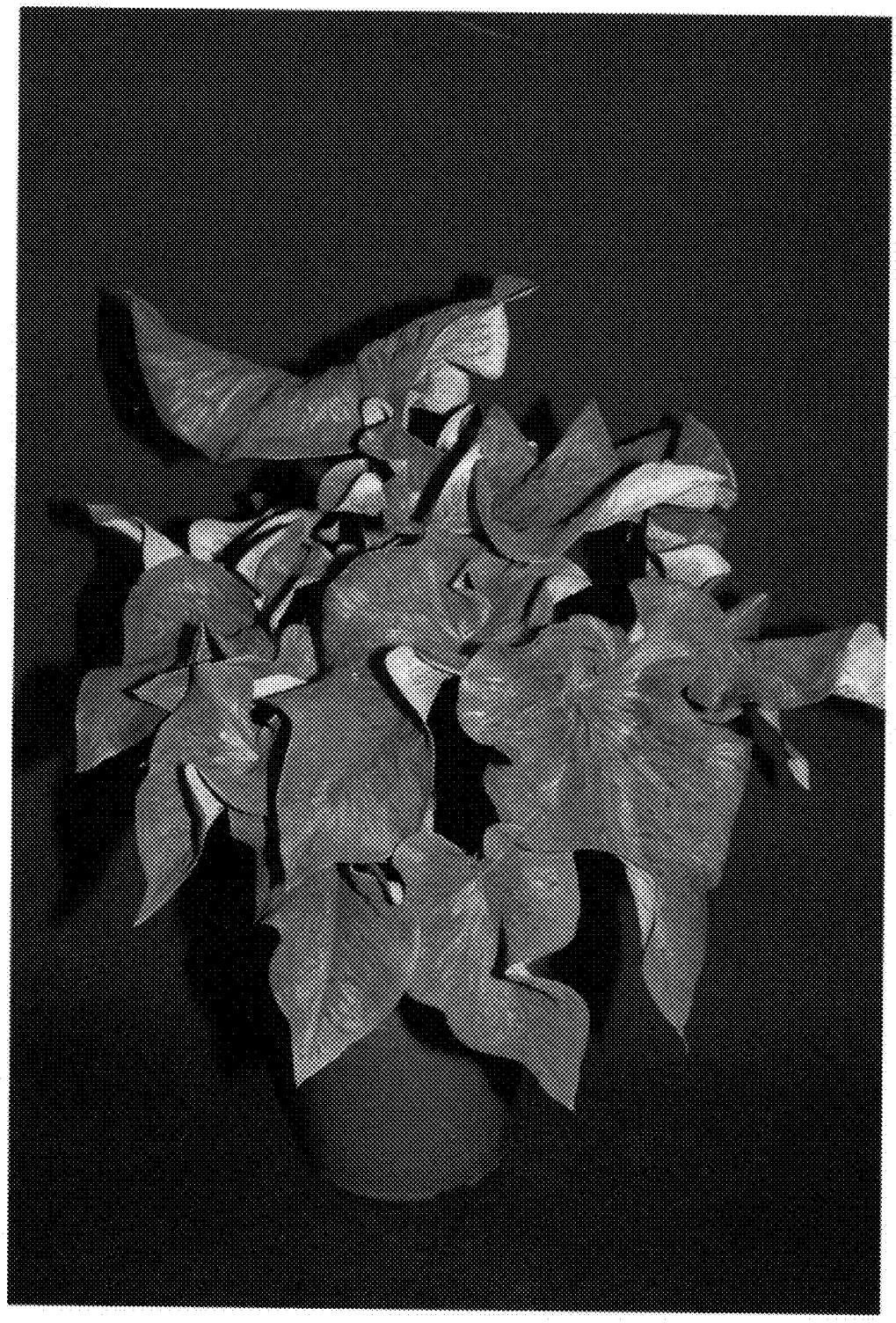

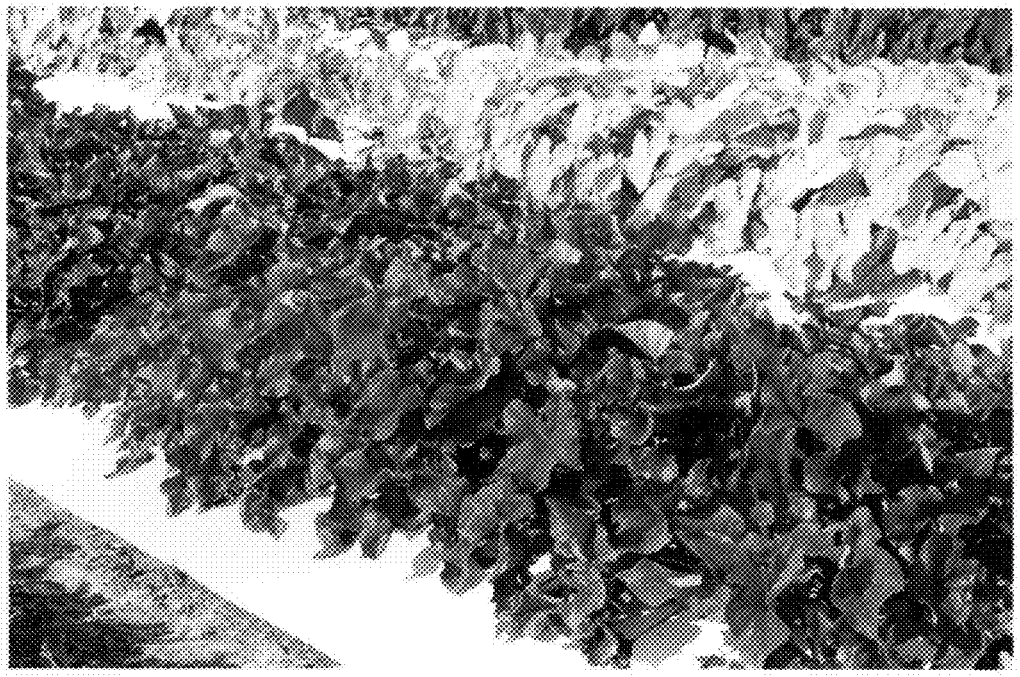
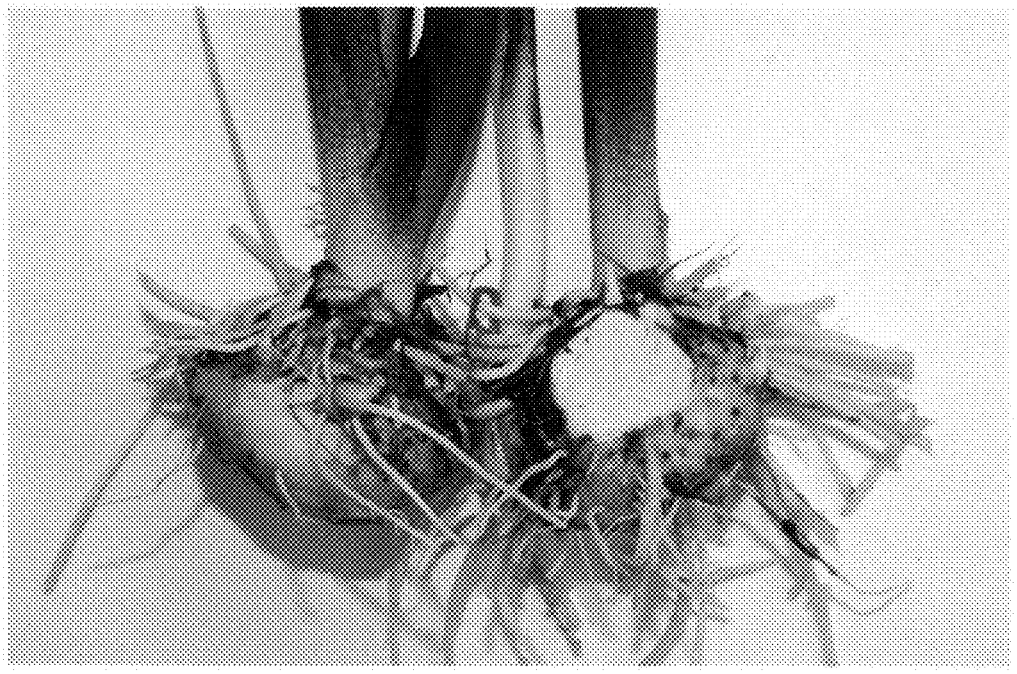

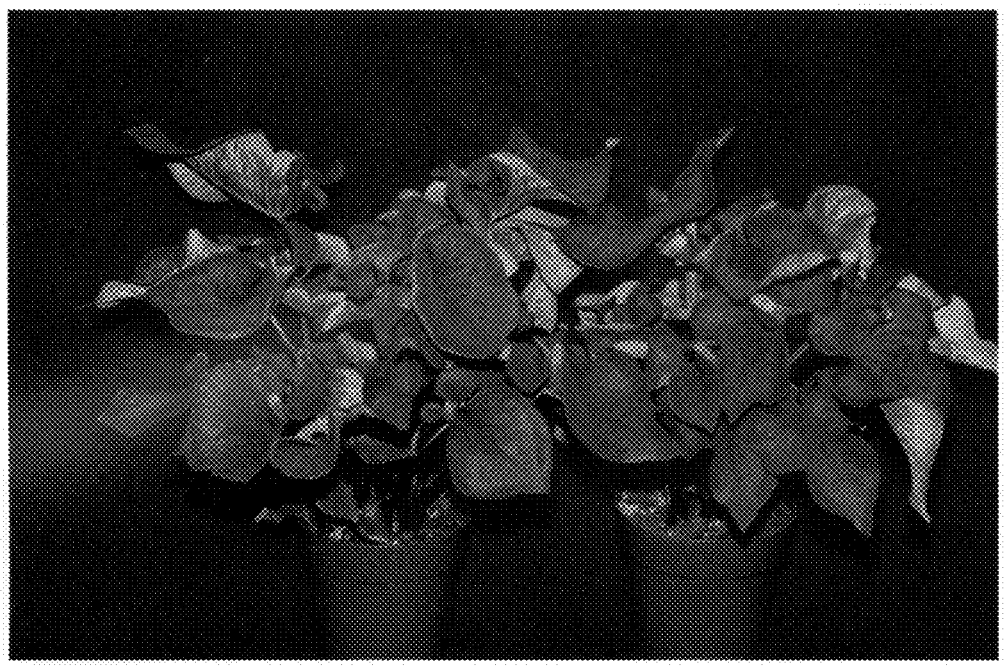
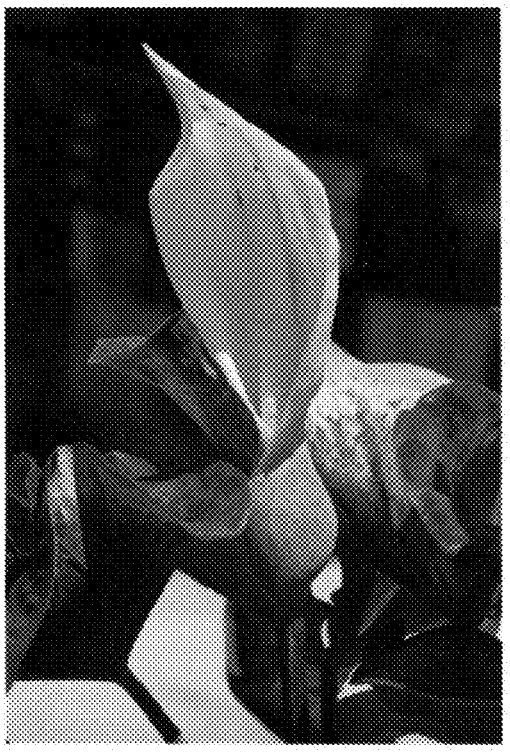

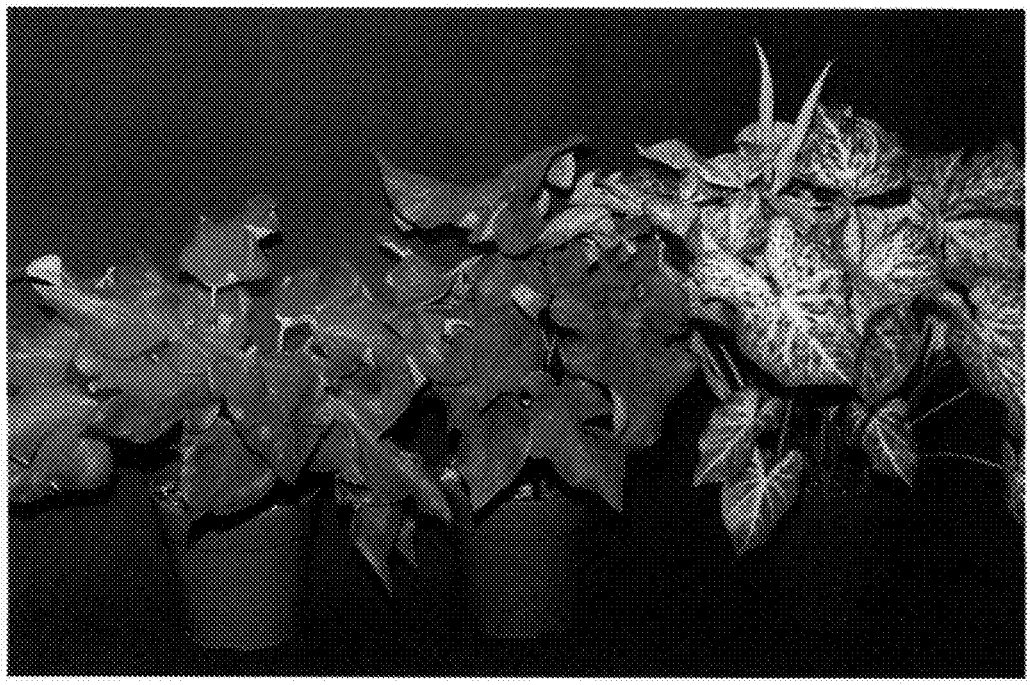
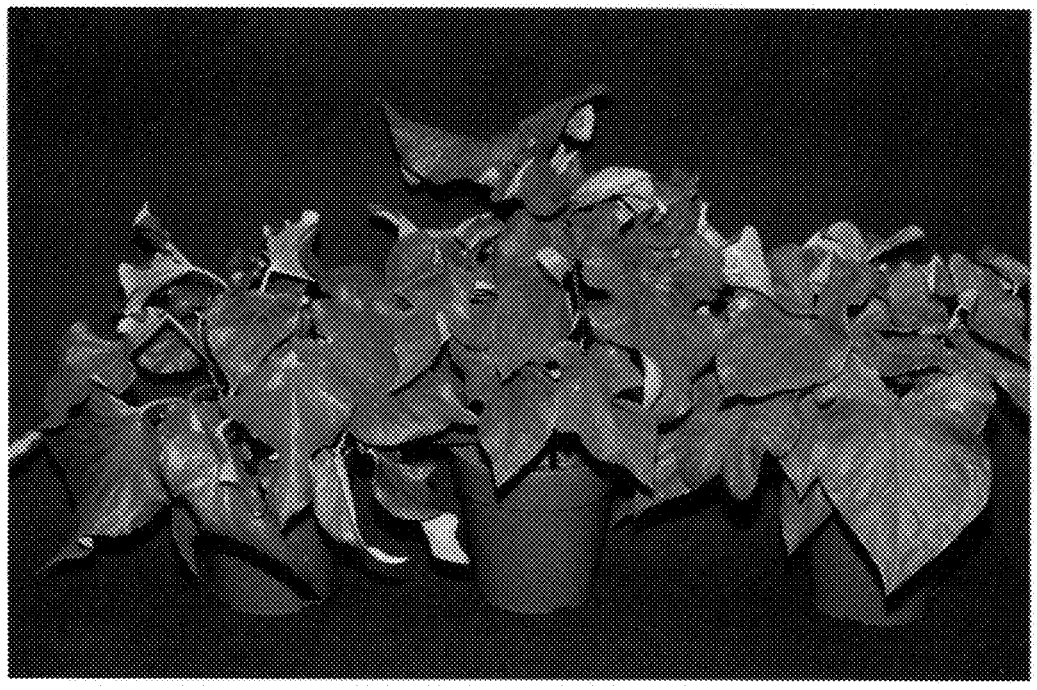

* * * * *